(12) United States Patent
Suzuki et al.

(10) Patent No.: US 6,419,809 B1
(45) Date of Patent: Jul. 16, 2002

(54) MINIATURE REFERENCE ELECTRODE (75) Inventors: Hiroaki Suzuki, Ibaraki; Masao Karube, Kanagawa, both of (JP)

(73) Assignee: Katayanagi Institute, Tokyo (JP)

( * ) Notice: Subject to any disclaimer, the term of this patent is extended or adjusted under 35 U.S.C. 154(b) by 0 days.

(21) Appl. No.: 09/535,906

(22) Filed: Mar. 24, 2000

(30) Foreign Application Priority Data

Jun. 24, 1999 (JP) ............................................. 11-177714

(51) Int. Cl.[7] ............................................. G01N 27/401
(52) U.S. Cl. ........................ 204/435; 204/402; 204/420
(58) Field of Search ................................ 204/402, 420, 204/435

(56) References Cited

U.S. PATENT DOCUMENTS

| 3,676,319 A | * | 7/1972 | Kirsten |
| 3,960,689 A | * | 6/1976 | Lanier |
| 4,031,606 A | * | 6/1977 | Szonntagh |
| 4,053,381 A | * | 10/1977 | Hamblen et al. |
| 4,454,007 A | * | 6/1984 | Pace |
| 4,857,166 A | * | 8/1989 | Kotani |
| 5,066,383 A | * | 11/1991 | Yamaguichi et al. |
| 5,126,034 A | * | 6/1992 | Carter et al. |
| 5,273,631 A | * | 12/1993 | Ohsawa et al. |
| 5,384,031 A | * | 1/1995 | Anderson et al. |
| 5,520,787 A | * | 5/1996 | Hanagan et al. |
| 5,571,395 A | * | 11/1996 | Park et al. |
| 5,714,045 A | * | 2/1998 | Lasa et al. |

* cited by examiner

Primary Examiner—T. Tung
(74) Attorney, Agent, or Firm—Seed IP law Group PLLC (57) ABSTRACT A miniature reference electrode with improved stability and durability formed of a miniature silver/silver chloride reference electrode with high stability and general applicability as a reference electrode. The miniature reference electrode includes, on electrode substrate, a thin-film backbone metal pattern and a thin-film silver pattern formed in electrical contact with a portion of the thin-film backbone metal pattern. A silver chloride layer is set on a portion of the thin-film silver pattern. The silver chloride layer is in contact with a portion of thin-film electrolyte layer via hydrophobic thin-film insulating layer. The thin-film electrolyte layer is impregnated with a saturated solution of potassium chloride for making contact to the outside via a thin-film liquid junction pattern. When in use, the thin-film liquid junction pattern (31) is impregnated with the electrolyte, while its end portion is recessed in an aqueous solution.

11 Claims, 10 Drawing Sheets

Liquid-junction reference electrode (type II). The indicated layers are sequentially formed. The dimensions of the chip are 1.5 mm x 13 mm.

Liquid-junction reference electrode (type II). The indicated layers are sequentially formed. The dimensions of the chip are 1.5 mm x 13 mm.

Durability of the thin-film Ag/AgCl element in saturated KCl, AgCl solution. The AgCl layer was formed at 3 μA for (a) 10 min, (b) 20 min, (c) 30 min, and (d) 40 min.

*Fig. 9*

Variation of the potential of the completed liquid-junction reference electrode. The experiment was conducted in unstirred 50 mM $KH_2PO_4$-NaOH buffer solution (pH 7.0).

*Fig. 10*

Dependence of the AIROF indicator electrode potential on pH. The potential was measured against the integrated miniature reference electrode (●) and the macroscopic reference electrode (○). The data were taken (a) 1 h and (b) 25 h after the start of the experiment. The chip was stored in unstirred 50 mM $KH_2PO_4$-NaOH buffer solution (pH 7.0).

*Fig. 11*

Response curve of the one-chip pH sensor.
Arrows indicate that NaOH was added to 0.1 M KCl/5 mM $KH_2PO_4$ solution successively.

Fig. 12

MINIATURE REFERENCE ELECTRODE

TECHNICAL FIELD OF THE INVENTION

The disclosed embodiments of the invention pertain to a miniature reference electrode for use in the chemical sensor or biosensor based on the electrochemical principle in many electrochemical experiments, and in particular, to a miniature silver/silver chloride reference electrode with high stability and general applicability as a reference electrode.

BACKGROUND OF THE INVENTION

A reference electrode is an electrode used as a reference in a potential setting or potential measurement. It is an important structural element indispensable not only in the basic studies of electrochemistry, but also in the application research of chemical sensors. For example, in cyclic voltammogram and other experiments with the electrode potential included as an information, there is a demand on a reference electrode that can provide a stable reference potential. Also, for the chemical sensors and biosensors, in particular, for the potentiometric sensors for potential measurement, the potential of the indicator electrode that measures the chemical substance is measured using the reference electrode as a standard, and the concentration of the chemical substance is measured with the potential as an index. Consequently, if a highly stable and reliable reference electrode is not used, the deviation in the potential leads directly to a measurement error.

Figure 1:
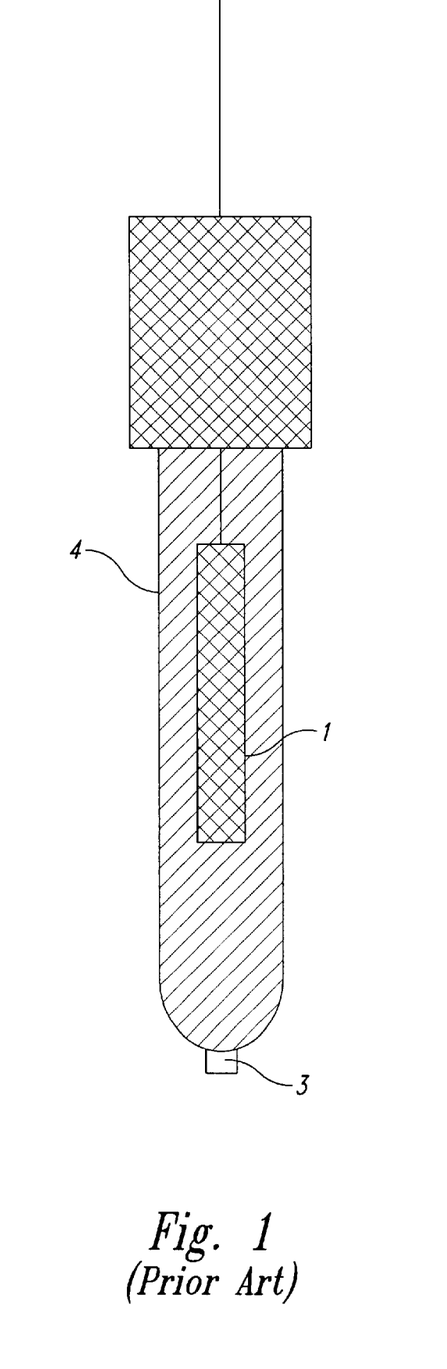
FIG. 1 is a diagram illustrating the structure of the conventional, commercially available silver/silver chloride electrode.

Consequently, the reference electrode is a basic and important element for the electrochemical sensor. At present, the silver/silver chloride electrode is most widely used as the reference electrode. The structure of the silver/silver chloride electrode is shown in FIG. 1. In container (4) made of glass, rod-shaped "silver/silver chloride" (1) is set. In the end portion of glass container (4), a liquid junction (3) made of a ceramic plug or the like is formed. The interior of the container (4) is filled with saturated KCl solution or saturated NaCl solution.

Figure 2:
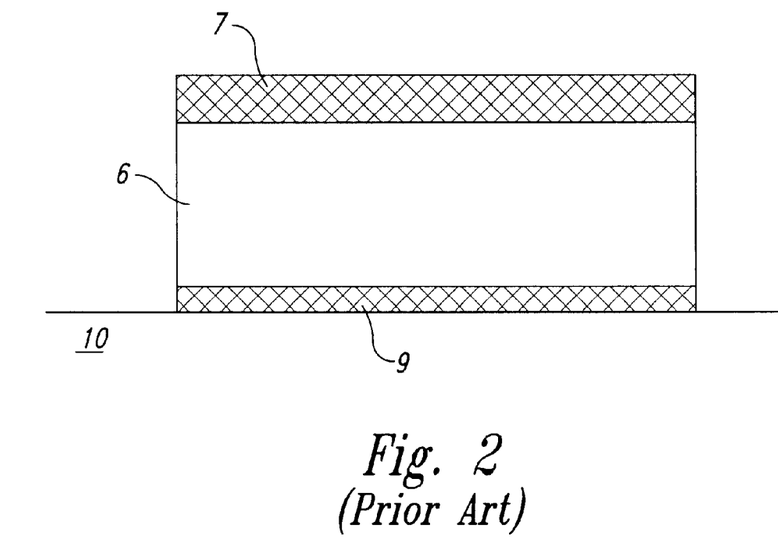
FIG. 2 is a diagram illustrating the structure of a conventional thin-film silver/silver chloride electrode.

In recent years, there has been progress achieved in miniaturizing the chemical sensors and biosensors. Consequently, there has been a demand for development of a miniature reference electrode that can provide a stable potential. The miniature silver/silver chloride electrode conventionally used to meet this demand is shown in FIG. 2. On substrate (10), base metal layer (9), silver layer (6) and silver chloride layer (7) are sequentially laminated, and "silver/silver chloride" is only in a simple thin film form.

For the thin-film silver/silver chloride electrode (FIG. 2) as the miniature reference electrode, the "silver/silver chloride" portion (the portion of silver layer (6) and silver chloride layer (7)) is prepared as follows. For example, silver layer (6) is formed on a layer of chromium or titanium as the adhesion layer (9). Its surface is partially converted to silver chloride. In certain cases, in order to further improve the adhesion property of silver, an intermediate layer made of gold or platinum or the like is included between adhesion layers (9) and silver [layer] (6) in consideration of the structure or process of the sensor. (Also, this structural body is usually formed by patterning with the aid of photolithography).

The thin-film silver/silver chloride electrode (FIG. 2) is usually used by placing it in direct contact with the sample solution. However, for the silver/silver chloride reference electrode, the electrode potential varies as a function of the active amount of chlorine ions. Consequently, in order to perform an appropriate measurement, it is necessary to use it in a solution having a predetermined active amount of chlorine ions. Consequently, when it is used in combination with a certain micro indicator electrode, a solution with a predetermined active amount of chlorine ions is prepared separately and brought into contact with the "silver/silver chloride" portion, and an appropriate amount of sample solution is added to perform the measurement.

However, in this prior method, each time it is used, one has to prepare a solution with a predetermined active amount of chlorine ions. Also, when the sample is injected, the active amount of chlorine ions varies a little, leading to unwanted variations in the potential. Also, in the case when a sample is measured without dilution as the level best for the practical application, it is very difficult to measure the active amount of chlorine ions beforehand, and the measurement value itself is unreliable.

Consequently, when measurement with a high reliability is to be carried out, as shown in FIG. 1, one must make the "silver/silver chloride" portion in contact with a saturated solution of KCl and make the connection to the outside through a liquid junction.

However, for the structural body of the thin-film silver/silver chloride reference electrode shown in FIG. 2, as it is a thin film, the silver chloride layer (7) is very thin. Consequently, the durability is low, and it is damaged in a time as short as a few minutes in a saturated solution of KCl. Consequently, there is yet no commercially available product using this structure directly (that is, the structure in which solution of KCl or NaCl in a saturated or nearly saturated concentration is filled as the internal electrolyte, and connection to the outside is performed by means of a liquid junction).

SUMMARY OF THE INVENTION

The disclosed embodiments of the present invention provide a miniature reference electrode with improved stability and durability. In particular, the embodiments of the invention provides a miniature silver/silver chloride reference electrode with high stability and general applicability as a reference electrode.

Figure 3:
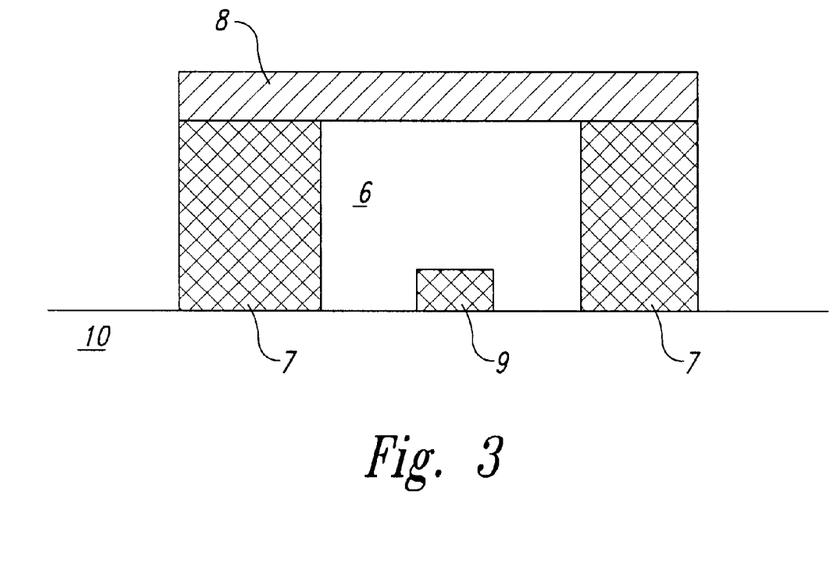
FIG. 3 is a diagram illustrating the structure of an improved thin-film silver/silver chloride electrode.

A "silver/silver chloride" structural body is shown in FIG. 3. It differs from a conventional product in that the surface of silver thin film (6) is covered with a water-repellent polymer layer (8) (for ease of reference, the same part numbers as in FIG. 2 are adopted here for similar elements), and silver chloride layer (7) is formed from the end portion of silver thin film (6) instead of from the surface of the thin film. It was found that the lifetime of the thin-film "silver/silver chloride" structural body in the saturated aqueous solution of KCl or AgCl was prolonged by nearly 300-fold. Thus, the thin-film "silver/silver chloride" structural body is used as the reference electrode having the liquid junction as explained above.

Figure 4:
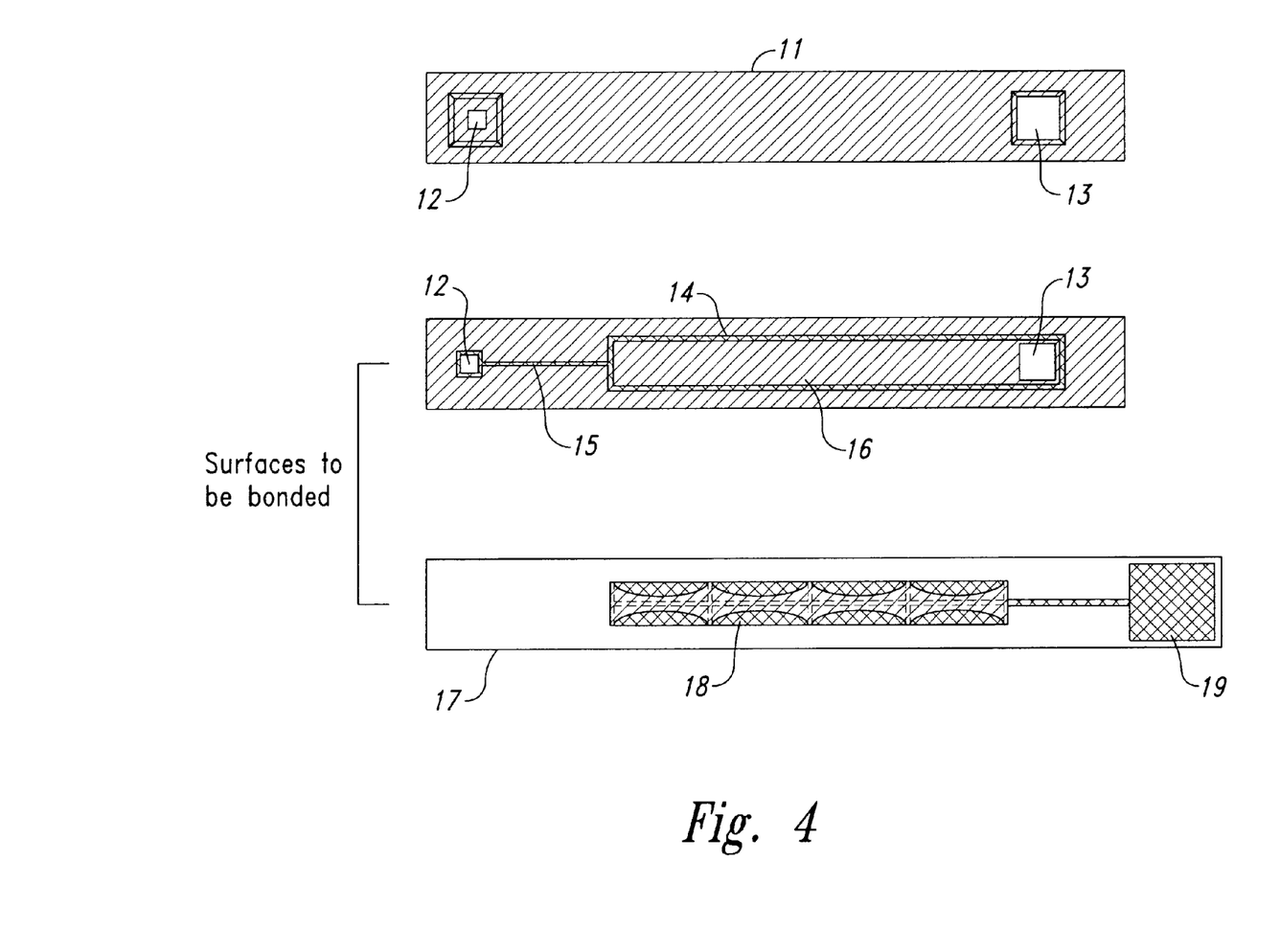
FIG. 4 is a diagram illustrating the structure of the silver/silver chloride electrode having liquid junction and developed by the present inventors.

The thin-film "silver/silver chloride" structural body can be manufactured as a reference electrode having a liquid junction (15) (FIG. 4). In this case, the container portion (16) for storing the electrolyte (saturated aqueous solution of KCl or AgCl) and liquid junction (15) arc formed on a silicon substrate (14), and it is bonded to a glass substrate (17). The thin-film "silver/silver chloride" structure (18) is thus formed.

For the reference electrode with a liquid junction, when it is in use, an electrolyte is injected from outside (11) of the silicon substrate through an electrolyte feeding port (13), the end portion of liquid junction (12) is recessed into a predetermined solution, and the portion of pad (19) is connected to a terminal for measurement. The reference electrode having the liquid junction shown in FIG. 4 can display the desired stable potential.

However, for the miniature reference electrode of the aforementioned prior art, there were several problems. The problems of the miniature reference electrode of the aforementioned prior art and the methods for solving them, more specifically, the problems that take place in company with setting of the aforementioned liquid junction and the methods for solving them, are as follows.

The first problem is as follows: When the electrolyte (KCl) is introduced as an aqueous solution, due to flow-out of KCl inside it and flow-in of water outside it, the concentration of KCl of the internal solution significantly decreases to a measurement error, and the lifetime becomes as short as a few hours. On the other hand, when more KCl is stored in a deposited state, this problem is expected to be improved, yet in the system in which the electrolyte solution is introduced later, such as the reference electrode shown in FIG. 4, as the size becomes smaller, it becomes extremely difficult. This problem can be solved by forming the layer of KCl or NaCl as the electrolyte in powder form without dissolution. More specifically, this problem is solved by the following method: KCl or NaCl powder as the electrolyte cannot be directly used to form an electrolyte pattern, it is dispersed in a paste prepared using an organic solvent, and the paste is applied by screen printing on the necessary sites, followed by dissipation of the solvent to form the desired electrolyte layer.

The next problem is as follows: For the liquid junction, if a structure in which a fine polymer layer is filled and flow-out of KCl is inhibited is not adopted, the internal KCl will be soon lost. This problem can be solved by the following method: A hydrophilic polymer film is used for the liquid junction, and, in order to suppress the flow-out rate of KCl, KCl is made to flow out in the direction perpendicular to the film's cross-section. (If the internal liquid flows out in the direction perpendicular to the film surface, the flow-out rate of KCl becomes higher).

The third problem is as follows: Degradation of 'silver/silver chloride' starts at the time when contact is made with the electrolyte. Consequently, it is preferred that the electrolyte solution be introduced right before use. However, for the reference electrode shown in FIG. 4, it is necessary to introduce the electrolyte solution by means of a degassing operation and centrifuge. Consequently, it is usually very difficult for conventional users. This problem can be solved by the following method: Since degradation of the thin-film 'silver/silver chloride' starts at the time when contact is made with the saturated aqueous solution of KCl, activation is carried out right before use. When this is implemented, the saturated solution of KCl or AgCl is made to pass through a passivation layer for injection by means of a microsyringe.

The miniature reference electrode of the disclosed embodiments herein has the following features.

The miniature reference electrode contains a thin-film backbone metal pattern set on an electrode substrate, a thin-film electrode metal pattern set on said thin-film backbone metal pattern and is in electrical contact with a portion of said thin-film backbone metal pattern, a metal salt region which is set on a portion of said thin-film electrode metal pattern and is made of the salt of the structural metal of said thin-film electrode metal pattern, a thin-film electrolyte layer which is a thin-film electrolyte layer impregnated with the saturated solution of electrolyte shared with the anionic portion of said metal salt region and which has a portion in contact with said thin-film metal salt layer via a hydrophobic thin-film insulating layer, and a thin-film liquid junction pattern which is in contact with a portion of said thin-film electrolyte layer and is prepared by impregnation with an electrolyte solution containing the electrolyte of said thin-film electrolyte layer; while the overall miniature reference electrode is covered with a protective film, at least a portion of said thin-film backbone metal pattern is exposed as the electrode terminal portion, and a portion of said thin-film liquid junction pattern is exposed as a contact portion with the external liquid.

The miniature reference electrode described above has a thin-film electrolyte layer with the electrolyte carried in the form of solid particles.

The miniature reference electrode in one embodiment, is formed so that the metal of said thin-film electrode metal pattern is silver, the metal salt of said metal salt region is silver chloride, and the electrolyte of said thin-film electrolyte layer is potassium chloride. The miniature reference electrode may have the metal of the thin-film backbone metal pattern formed of gold.

The miniature reference electrode described above may have a plurality of holes formed on the thin-film electrode metal pattern, and, as the hydrophobic thin-film insulating layer is bonded with said electrode substrate through the holes, the adhesion of the thin-film electrode metal pattern on the electrode substrate is increased.

A one-touch potentiometric sensor may be formed using the miniature reference electrode described above and a sensor based on the potentiometric measurement principle that are integrated in a single step.

A one-touch electrochemical measurement system is provide, with a function electrode, a counter electrode, and the miniature reference electrode described above integrated on a single chip.

The miniature reference electrode has the electrode substrate, and an auxiliary electrode pattern is set on the electrode substrate via another metal pattern and a thin-film insulating layer.

A method for prolonging the lifetime of the miniature reference electrode made of plural thin-film layers is also disclosed. The method includes, in the miniature reference electrode made of plural thin-film layers, forming a portion of a thin-film electrode metal pattern to have a metal salt region made of the salt of the structural metal of the thin-film electrode metal pattern, and the metal salt region is exposed on the surface of the thin-film electrode metal pattern; a portion of said metal salt region is a thin-film electrolyte layer impregnated with the saturated solution of an electrolyte shared with the anionic portion of said metal salt region, and it is in contact with a portion of the thin-film electrolyte layer which has said electrolyte carried in the form of solid particles; and a portion of said thin-film electrolyte layer is liquid junctioned to the outside.

In accordance with another embodiment of the invention, a miniature silver/silver chloride reference electrode is provided which includes: on a substrate, a pattern made of a noble metal and acting as a backbone; a silver pattern is formed such that it makes contact with a portion of the noble metal pattern; an insulating layer that does not allow permeation of aqueous solution is covered on the entire surface of the silver pattern and the portion other than the pad portion; on the silver pattern, an opening is formed in said insulating layer; a silver chloride layer is formed from the slit through the interior of the silver pattern; also, a hydrophilic porous layer as the liquid junction is formed; a hydrophilic porous layer containing particles of chlorine-containing salt and electrolyte solution is formed such that the slit and the liquid junction pattern are contained; and a protective film that does not allow permeation of the aqueous solution is formed such that a portion of the liquid junction and the pad portion is left, and at least the entire region of the hydrophilic porous layer that contains the particles of chlorine-containing salt and electrolyte solution, is covered.

BRIEF DESCRIPTION OF THE FIGURES

The embodiment of the invention described herein will be better understood when taken in conjunction with the following drawings, wherein.

DETAILED DESCRIPTION OF THE INVENTION

According to the disclosed embodiments of the invention, the electrode can be manufactured using the fine processing technology related to semiconductor devices. In particular, it is preferred that the electrode be manufactured using the lithographic technology by means of photocuring resin.

When used throughout the specification, "a portion" may also mean plural sites known as "portions," as long as the main features of this invention are observed. Also, "a portion" includes the case when "a portion" is formed from another member when said another member is formed on certain member in a separate way (for example, when a silver chloride layer is formed on a portion of the silver layer), the case when a portion of certain member is substituted with another member to form "a portion" made of said another member (for example, when a portion of the silver layer is substituted with a silver chloride layer), and the case when a portion of a certain member is converted by chemical change to another member so that "a portion" made of said another member is formed (for example, when a portion of the silver layer is chlorinated so that said portion becomes a silver chloride layer).

"Thin-film liquid junction pattern" can be formed by using a hydrophilic porous resin.

In "hydrophobic thin-film insulating layer" and "protective film," it is preferred that a water-repellent polymer be used.

Also, in this specification, "thin film" is used in a concept as different from the centimeter-order members that forms the conventional electrode, and it usually means a layer formed by means of fine processing. Consequently, it includes both the micron-order thin film in the industry of fine processing and the 1/10-mm-order [film] known as "thin film" in this industry (for example, the insulating layer and protective film can be classified as "thick films" in the fine processing industry).

"Noble metal" refers to gold, platinum, and the like.

"Thin-film liquid junction pattern" refers to impregnation with an electrolyte solution. It includes both the case when it is impregnated with electrolyte solution and the case when there is a possibility of impregnation (presence of a container in a certain form that allows impregnation with the electrolyte solution).

"Carrying of electrolyte in the form of solid particles directly" means that the electrolyte is kept in a certain form, yet the specific form is irrelevant.

APPLICATION EXAMPLE 1

Referring to FIGS. 5a through 5e and 6a and 6b, the method for preparing the miniature silver/silver chloride reference electrode for one chip in Application Example 1 will be explained. However, plural miniature silver/silver chloride reference electrodes may be formed together on a single substrate (the same for Application Example 2 and thereafter).

Cleaning of Substrate

A 7740 glass substrate (20) (3 inches in diameter, 500 μm in thickness) was washed in a 1:1:4 heated mixture of 31% aqueous solution of hydrogen peroxide, 29% ammonia water and pure water, and then rinsed in heated pure water.

Formation of Backbone Pattern

Figure 5A:
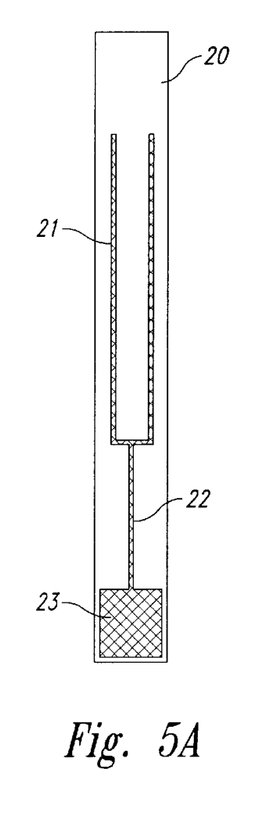
FIGS. 5a through 5e are diagrams illustrating the process in preparing the miniature silver/silver chloride reference electrode of Application Example 1.

On said glass substrate (20) prepared above, gold pattern (21) was formed as the backbone of the silver/silver chloride configuration. First of all, by means of sputtering, a chromium layer with a thickness of 40 nm and a gold layer with a thickness of 300 nm were formed sequentially on the entire surface of substrate (20). Then, by means of a positive photoresist (OFPR-800 manufactured by Tokyo Oka K.K.), patterning is performed, followed by etching of gold in a gold etching solution (prepared by dissolving 10 g potassium iodide and 2.5 g iodine in 100 mL pure water). After etching, the resist was peeled off in acetone, followed by washing thoroughly and drying in acetone.

Then, substrate (20) was recessed in a chromium etching solution (prepared by dissolving 25 g potassium ferricyanide and 12.5 g potassium hydroxide in 100 mL pure water) to remove the chromium layer. Then, after etching, substrate (20) was washed thoroughly with pure water, followed by drying with dry nitrogen gas.

In this way, the backbone pattern was completed (FIG. 5(a)). The metal material used in this case is not limited to gold. Platinum or other noble metals with high resistance to the electrode reaction may also be used.

Formation of Lift-off Pattern for Silver

On the substrate with gold-pattern backbone (21) formed above, a pattern for lift-off was formed by a positive photoresist (manufactured by Shipley). First of all, after the positive photoresist is spin-coated on the substrate, baking was performed at 80° C. for 30 min. Then, a photomask of the desired pattern was used for exposure, followed by recessing in toluene at 80° C. for 5 min, then drying and baking at 80° C. for 15 min. Then, development was performed in a developing solution at 30° C., followed by rinsing in pure water and blowing with dry nitrogen gas to dry.

Formation of Silver Thin Film

Figure 5B:
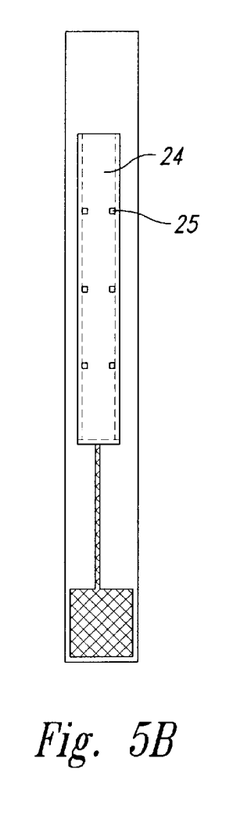
Figure 5C:
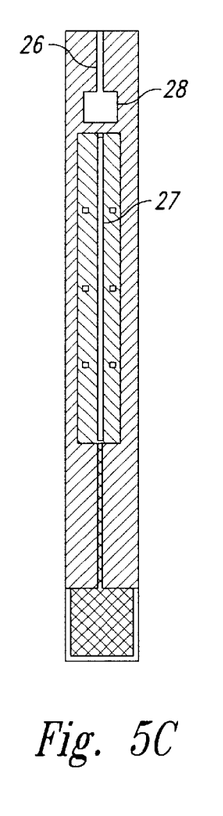
Figure 5D:
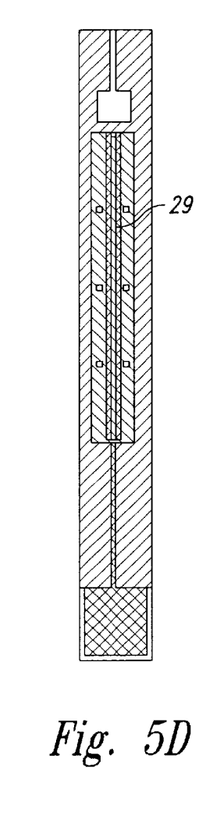

Silver thin film (24) with a thickness of 300 nm was formed by sputtering.

Lift-off

The substrate with silver thin film sputtered above was recessed in acetone to dissolve the resist, so that silver thin film (24) on the resist pattern was lifted off. Then, after cleaning well using clean acetone, drying was performed using dry nitrogen (FIG. 5(b)).

Formation of Water-repellent Polymer Layer

Polyimide layer was used as water-repellent polymer layer (26). In this case, polyimide prepolymer (Photoneese [transliteration] UR-3140, product of Toray Industries, Inc.) was coated. After baking at 80° C. for 1 h, exposure was performed. Then, curing was performed at 150° C. for 30 min, at 200° C. for 30 min, and at 300° C. for 1 h. After curing the film thickness was 10 $\mu$m. Also, on polyimide layer (26), recess (28) for flowing-in of the hydrophilic polymer layer for liquid junction, slit formed on silver pattern (24), and opening for exposing the vicinity of pad (electrode terminal portion) (23) are formed (FIG. 5(c)).

Dicing of Substrate

The chip of the miniature reference electrode was cut out using a dicing saw.

Formation of Silver Chloride Layer

The vicinity of the portion where silver was formed on the chip of the miniature reference electrode cut out above was immersed together with a platinum plate in a KCl—HCl buffer containing 1 M KCl (pH 2.2, 25° C.), and a constant current of 3 $\mu$A was made to flow for 40 min so that silver chloride layer (29) was formed from near slit (27) on silver thin film (24). After formation, the chip was cleaned with pure water and then dried. In this operation, the miniature "silver/silver chloride" structure was completed (FIG. 5(d)).

In this case, at the site where silver chloride layer (29) is formed, the adhesion between silver chloride (29) and substrate (20) or polyimide (26) degrades, and silver chloride may be easily eluted from here, so that the lifetime becomes shorter. In order to solve this problem, as shown in FIG. 5a, through hole (25) is formed on the silver (or silver chloride) pattern, so that polyimide layer (26) and substrate (20) are bonded to each other through this hole, and silver chloride layer (29) is tightly pressed.

Formation of Liquid Junction

Figure 5E:
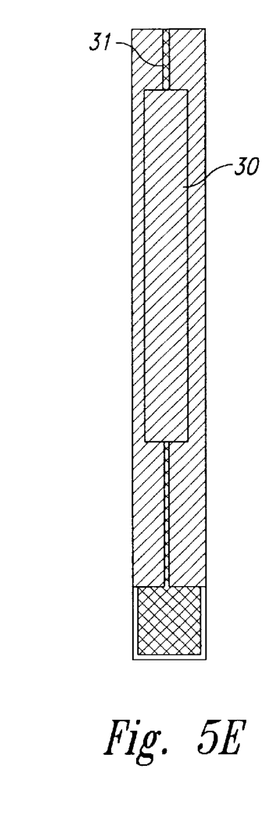

A hydrophilic polymer layer was formed as liquid junction (31) in recess (28) on the polyimide layer. As the hydrophilic polymer layer, ENT-2000 (product of Kansei Paint Co., Ltd.). First of all, a prepolymer of ENT-2000 was made to flow into recess (28) on the polyimide layer, curing was performed by irradiating light emitted from a chemical lamp for 10 min.

Recess (28) was formed on polyimide layer (26), and said ENT was made to flow into it so as to form liquid Junction (31). Also, it is possible to apply the ENT pattern by means of screen printing followed by curing, instead of forming recess (28) on said polyimide layer (26). The feed material used as liquid junction (31) is not limited to said ENT. Any feed material may be used as long as it is hydrophilic and porous. For example, one may also make use of poly HEMA, porous silicone, etc. However, as the feed material determines the flow-out rate of KCl from the interior, although the feed material should be porous, sponge, or other materials having a large space so that electrolyte solution can flow at will cannot be used.

Formation of Electrolyte Layer

For the device size of the miniature reference electrode in this invention, the absolute amount of KCl in the internal electrolyte significantly affects the lifetime. Consequently, as long as it is possible, KCl should be introduced in deposited state, and electrolyte layer (30) containing fine powder of KCl was formed by screen printing to cover the entire region of said slit (27) and a portion of liquid junction (31). Also, electrolyte paste (30) in this application example comprised 0.15 g polyvinyl pyrrolidone (PVP), 450 $\mu$L of 2-propanol, and 1.2 g of fine powder of KCl.

Formation of Protective Layer

With a portion of liquid junction (31) left there, passivation layer (44) made of silicone rubber was formed. This was carried out by coating and curing the silicone rubber (a product of Shin-Etsu Chemical Co., Ltd.) except the liquid junction end portion and the vicinity of pad (33).

When mass production is performed for miniature reference electrodes, it is preferred that the order be re-arranged so that formation of the silver chloride layer is also carried out in wafer shape all at the same time. In this case, the electrode pattern is all connected at the site of the pad, and the portion where the electrode reaction is undesired is covered with a positive photoresist. Connection is made from one end of the wafer to the potentiostat, and the same operation as above may be carried out.

Introduction of Moisture and Activation

When used, saturated solution of KCl or AgCl was introduced into each chip to activate the miniature silver,/silver chloride. This can be carried out by means of a micro-syringe piercing through protective layer (44) to introduce a predetermined amount.

Also, for the miniature silver/silver chloride reference electrode in Application Example 1, the structure is such that a saturated solution of potassium chloride is filled in the container and the inter-liquid potential difference in the liquid junction portion can be removed. Consequently, for the solution used, there is no need to have a constant concentration of the chlorine ions.

APPLICATION EXAMPLE 2

Preparation of Miniature Reference Electrode

Figure 7A:
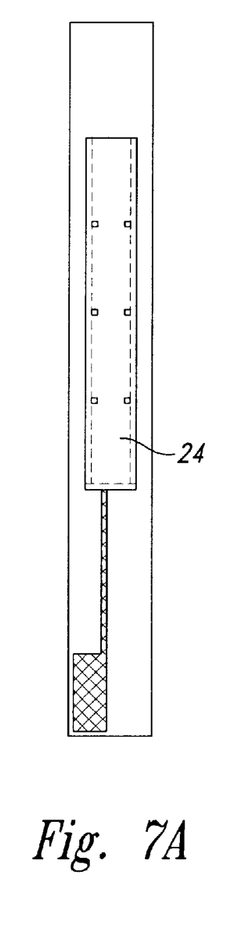
FIGS. 7a through 7c are diagrams illustrating the process in preparing the miniature silver/silver chloride electrode of Application Example 2.
Figure 7B:
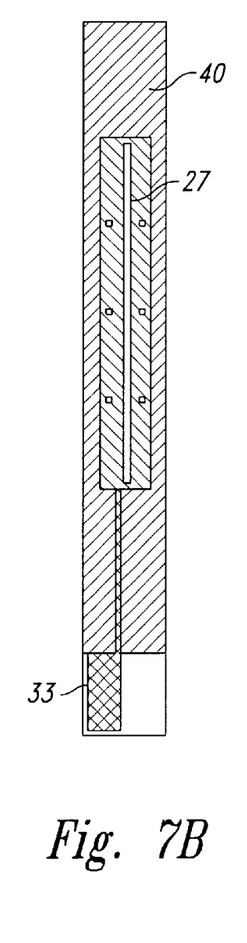
Figure 7C:
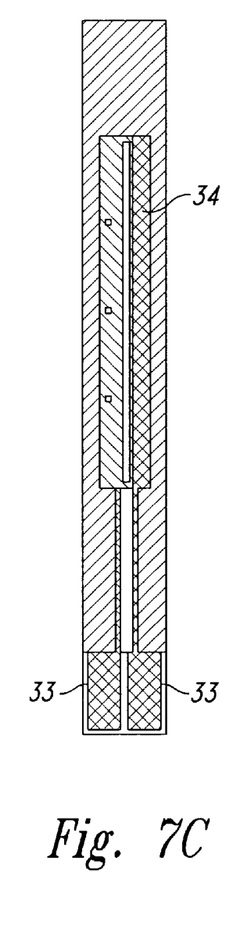

As shown in FIGS. 7a–7c, in the same way as in the first five steps in Application Example 1, metal backbone (21) and silver layer (24) in contact with a portion of it were formed.

Formation of Insulating Layer

On the substrate in said (1), a laminated structure made of SiO$_2$ layer (40) was formed by means of CVD. Also, in this case, on the silver pattern, slit (27) was formed and the vicinity of pad (33) was exposed just as in Application Example 1.

Formation of Auxiliary Electrode Pattern

Just as in the third step of Application Example 1, a positive photoresist pattern was formed for forming platinum pattern (34) as the auxiliary electrode by means of lift-off.

Sputtering Formation of Platinum Layer

On the entire surface of the substrate with the lift-off pattern formed above, a platinum thin film (34) was formed by sputtering with a thickness of 300 nm.

Lift-off

The substrate prepared above was immersed in acetone to dissolve the resist, and the platinum this film on the resist pattern was lifted off. Then, after cleaning thoroughly with clean acetone, it was dried with dry nitrogen.

Formation of Silver Chloride Layer, Liquid Junction, Electrolyte Layer, and Protective Layer In the same way as in Application Example 1, the silver chloride layer, liquid junction, electrolyte layer, and protective layer were formed.

Introduction of Electrolyte Solution and Activation

Introduction of electrolyte solution and activation were carried out in the same way as in the final step of Application Example 1.

When this reference electrode is used, a minute current always flows between the silver/silver chloride electrode and the auxiliary electrode. In this way, while the silver chloride layer is dissolved, it is supplemented a little at a time, so that the lifetime of silver/silver chloride can be prolonged. When it is used in a potentiometric sensor, while such minute current flows, the potential between the silver/silver chloride electrode and the indicator electrode is measured.

APPLICATION EXAMPLE 3

Preparation of Miniature Silver/silver Chloride Reference Electrode

Figure 8A:
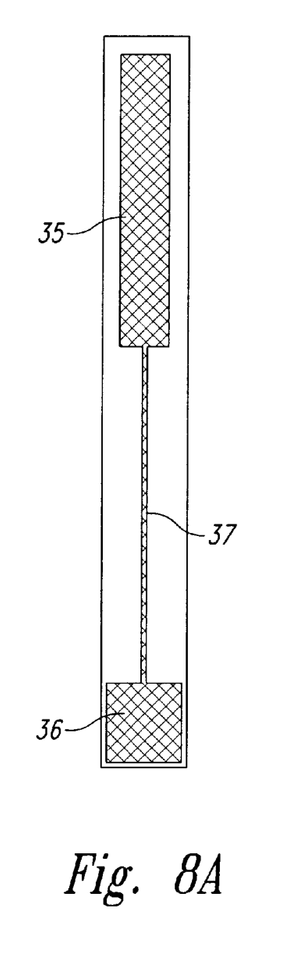
FIGS. 8a through 8c are diagrams illustrating the process in preparing the miniature silver/silver chloride electrode of Application Example 3.
Figure 8B:
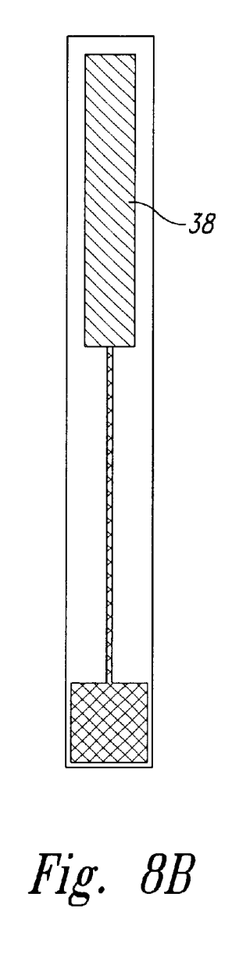
Figure 8C:
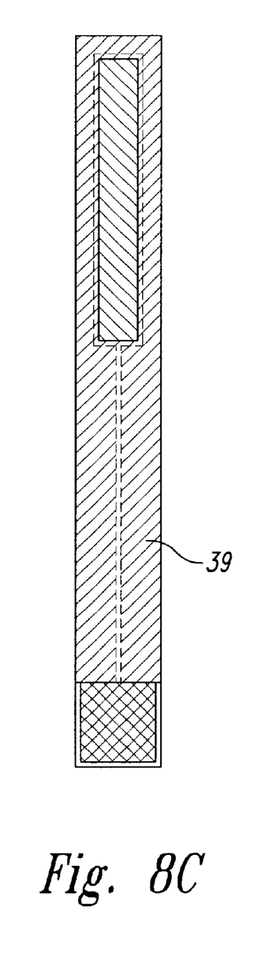

In the same way as in Application Example 1, a miniature silver/silver chloride reference electrode was prepared as shown in FIGS. 8a–8c. No electrolyte solution was introduced until completion of all of the following steps of operation.

Cleaning of the Substrate

Another glass substrate different from that on which the miniature reference electrode was formed was prepared separately, and the 7740 glass substrate (3 inches in diameter, 500 μm in thickness) was washed in a 1:1:4 heated mixture of 31% aqueous solution of hydrogen peroxide, 29% ammonia water and pure water, and then in heated pure water.

Formation of Backbone Pattern

In the same way as in step two of Application Example 1, on the glass substrate prepared above, a gold pattern (35) was formed as a backbone.

Formation of Lift-off Pattern for Iridium

In the same way as in step three of Application Example 1, a positive photoresist (product of Shipley Co.) was used to form a pattern for lift-off.

Formation of Iridium Layer

By means of sputtering, iridium layer (38) was formed with a thickness of 300 nm.

Formation of Upper Polymer Layer

On the substrate with iridium pattern (38) formed above, a polyimide prepolymer (PhotoneeseUR-3140, product of Toray Industries, Inc.) was coated. After baking for 1 h, exposure was performed. Then, curing was performed at 150° C. for 15 min, at 200° C. for 15 min, and at 300° C. for 30 min. After curing the film thickness was 4 μm. Also, with the 100-μm vicinity of iridium pattern (38) covered with polyimide layer (39), a portion of pad (36) was exposed.

TEST EXAMPLES

Stability of Thin-film Silver/Silver Chloride in Saturated Solution of KCl

Figure 9:
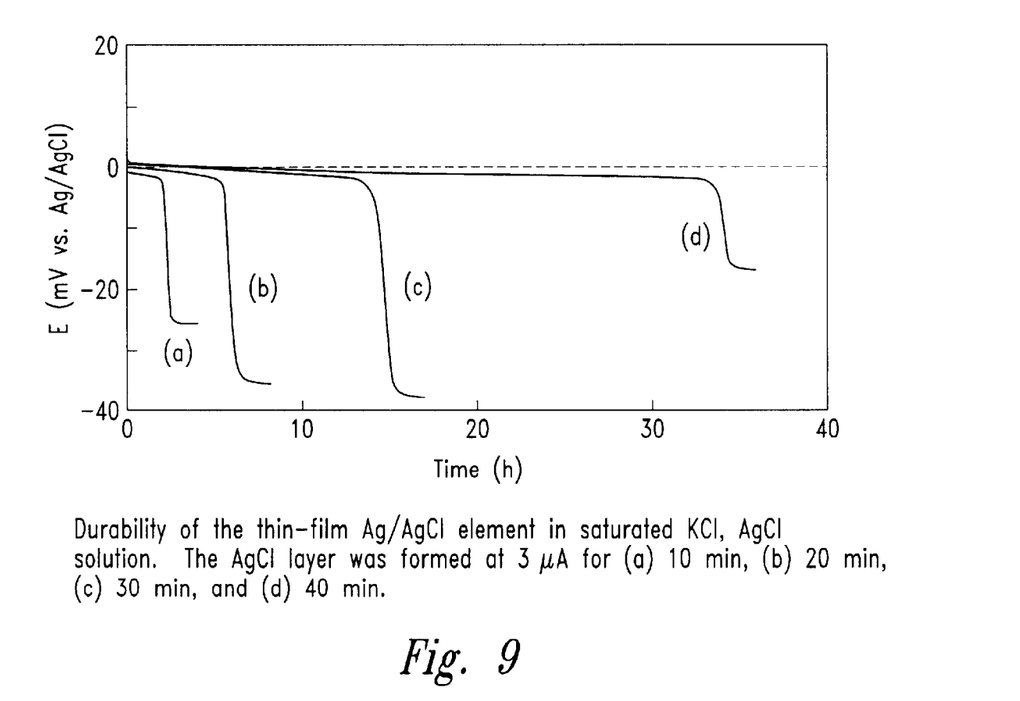
FIG. 9 is a diagram illustrating the results of the test on the stability of the miniature silver/silver chloride reference electrode of Application Example 1 in saturated aqueous solution of KCl or AgCl. In the figure, silver chloride layer (20) was formed at 3 μA for 10 min (a), 20 min (b), 30 min (c) and 40 min (d), respectively.

FIG. 9 illustrates the variation in potential of the thin-film silver/silver chloride used in the test in saturated Solution of KCl or AgCl. With growth of the silver chloride layer, the time in which the potential expected on silver/silver chloride can be maintained was prolonged. For the unit which had about 80% converted to silver chloride in 40 min during formation, a stable potential was maintained for longer than 30 h. In all of the cases, finally, there was a significant change in the potential in the negative direction, and the units are damaged. The same test was performed for a conventional silver/silver chloride electrode with conversion to silver chloride performed uniformly over then entire region of the surface of the silver thin film. It was found that the function could only last for 6 min. Consequently, the new structure displayed a significantly higher durability than the conventional structure.

Potential Stability of the Reference Electrode with Liquid Junction

Figure 10:
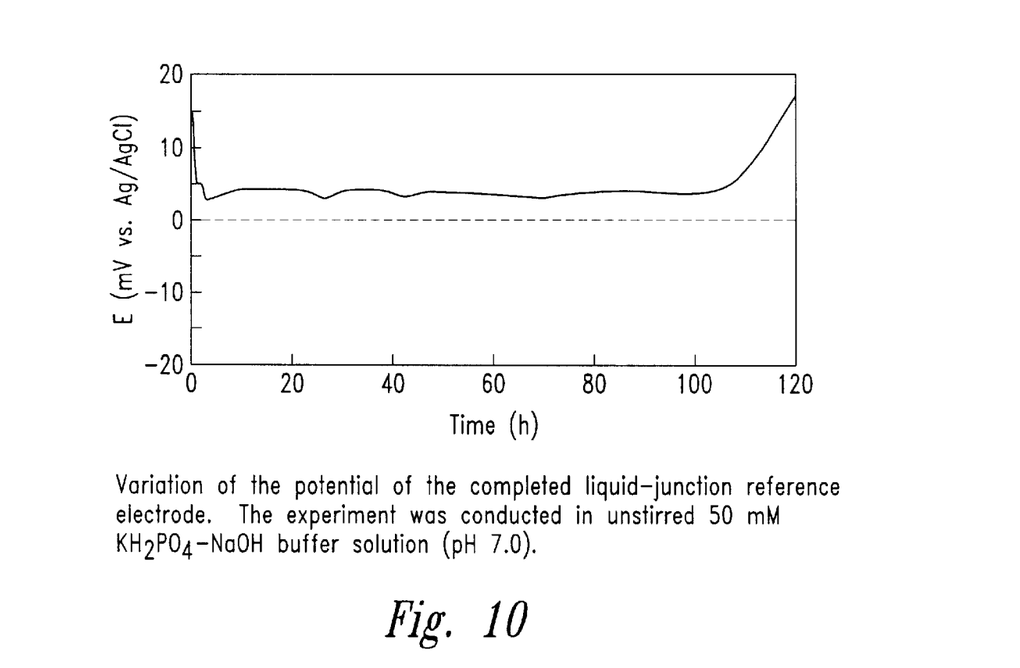
FIG. 10 is a diagram illustrating the variation over time of the potential of the miniature silver/silver chloride reference electrode of Application Example 1 in a 50-mM buffer solution of $KH_2PO_4$—NaOH without stirring (pH 7.0).

FIG. 10 is a diagram illustrating the variation over time of the potential of the reference electrode with liquid junction prepared in the above. It can be seen that for the silver/silver chloride electrode, the desired potential can last 100 h or longer. For the data shown here, when the lifetime is reached, the potential shifts in the + direction. This is clearly the Nernst response with respect to Cl that is reduced in company with dilution of the internal solution. In this way, it bears out the fact that the stable potential maintained up to this moment is due to silver/silver chloride. The variation in the potential during the period from start of a stable potential to start of rise in the potential when the lifetime is reached is within ±1.5 mV. Also, at each moment, the fluctuation in the potential is 0.1 mV or smaller. Compared with FIG. 9, it is believed that the lifetime of the thin-film silver/silver chloride electrode is further prolonged. It is believed that this is due to the fact that PVP used as the carrier of the electrolyte paste can suppress the dissolution of the silver chloride layer more effectively.

External KCl Concentration and pH Dependence

According to the results of studies on the dependence of the potential of the miniature reference electrode on the external KCl concentration indicate no significant dependence. In this way, it is found that the Nernst response of the silver/silver chloride body itself due to Cl⁻ is completely cancelled. Similarly, there is no dependence of the potential of the miniature reference electrode on pH.

One-touch Unit of pH Indicator Electrode

Figure 11:
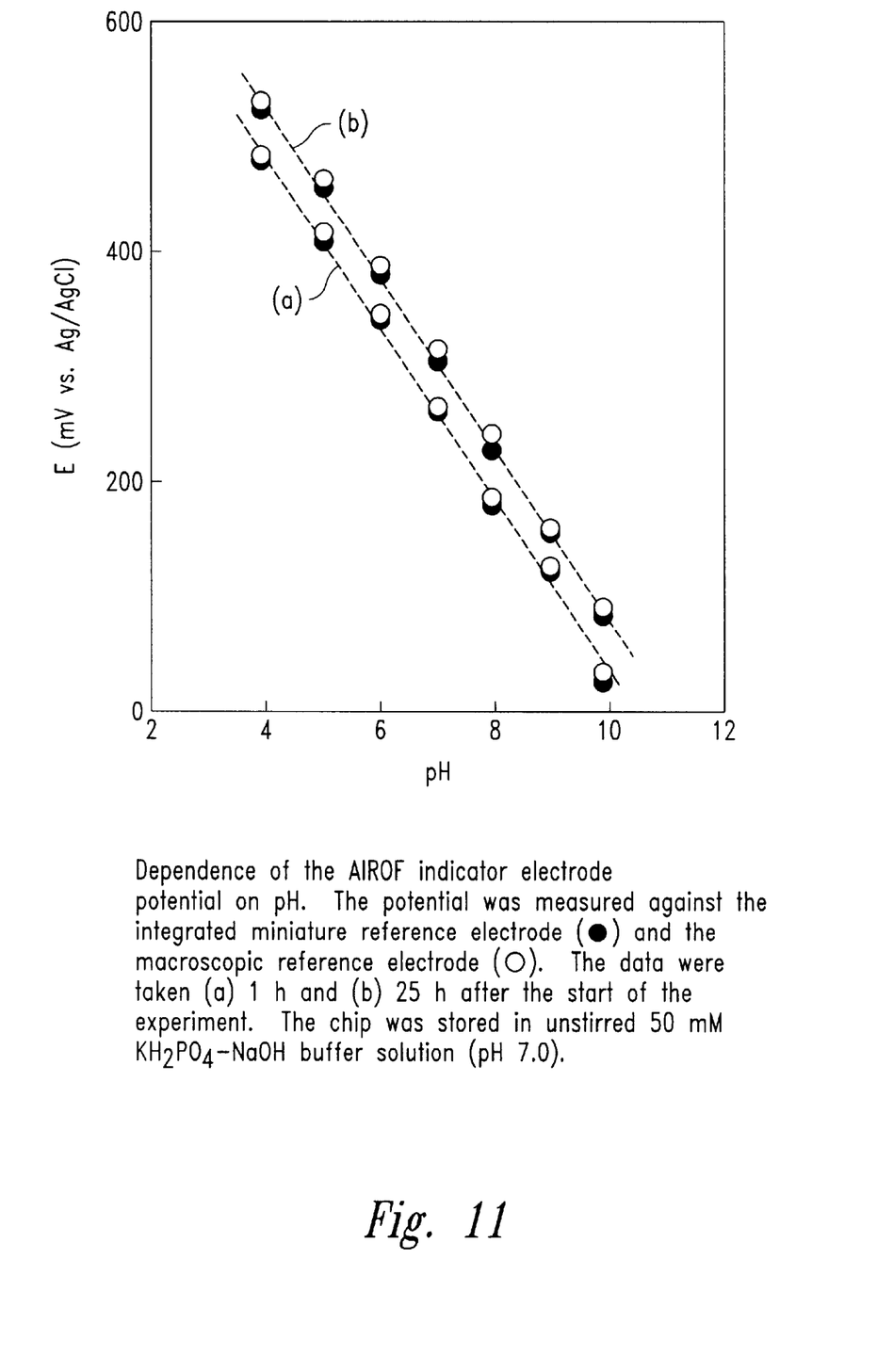
FIG. 11 is a diagram illustrating the results of measurement of the potential of the pH indicator electrode of iridium oxide film in a 50-mM buffer solution of $KH_2PO_4$—NaOH without stirring (pH 7.0), after immersing for 1 and 25 h in the external solution, respectively. Dots refer to the integrated miniature reference electrode used in the measurement, while circles refer to the micro reference electrode used in the measurement.
Figure 12:
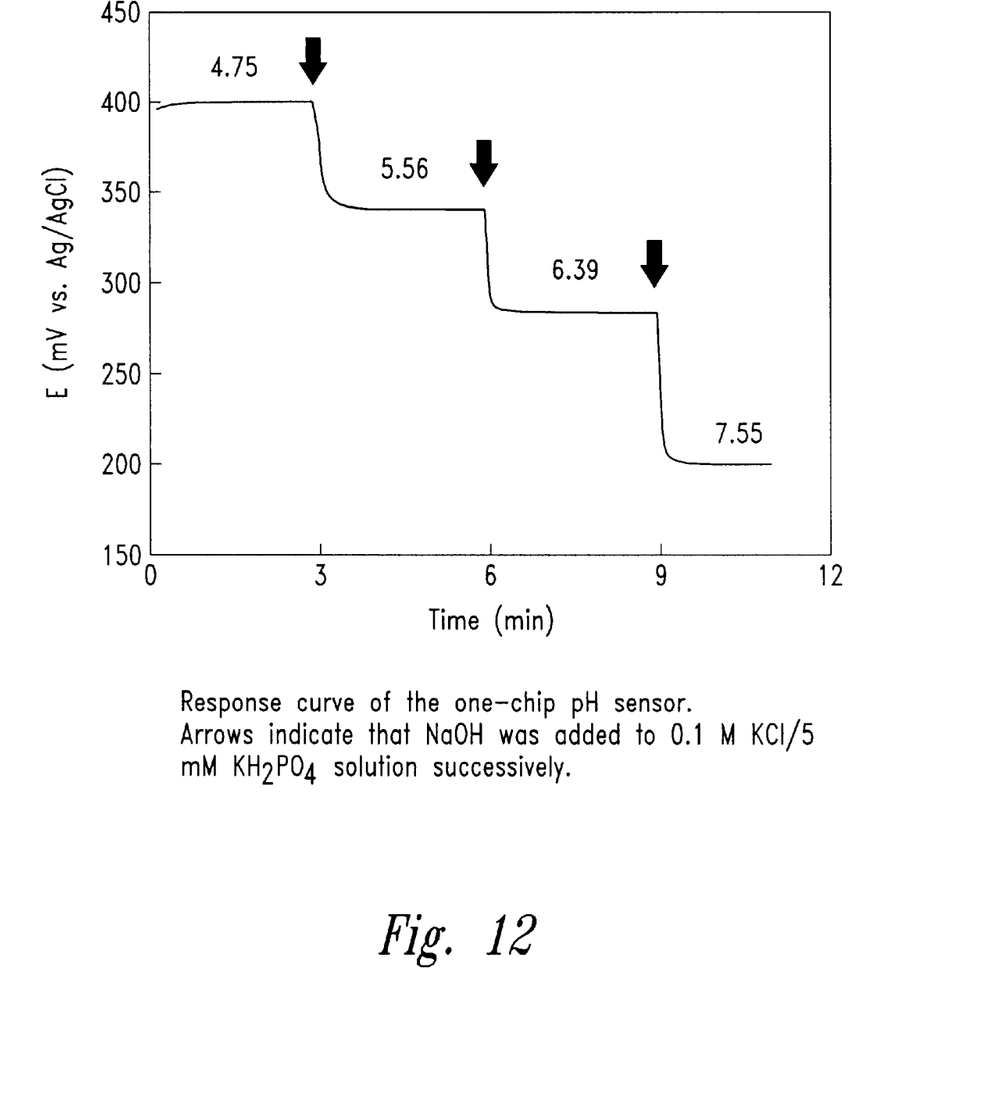
FIG. 12 is a diagram illustrating the response curve of the one-touch pH sensor with respect to pH curve measured by adding NaOH into 0.1 M KCl/6 mM $KH_2PO_4$ solution.

Using an integrated miniature reference electrode and micro reference electrode, after immersion and storage in an external solution, the potential of the pH indicator electrode of iridium oxide film was measured after 1 h and after 25 h, respectively, and the results were compared (see FIG. 11). The potentials of the indicator electrode with these references as standards are in good agreement with each other, bearing out the results described above. The deviation in the potential measured at the two times clearly indicates the variation over time on the side of the indicator electrode. Also, FIG. 12 is a diagram illustrating the response curve of the one-touch pH sensor with respect to variation in pH. It can be seen that the response is stable and clear.

USE EXAMPLE

The miniature silver/silver chloride reference electrode of this invention can be used in the electrochemical measurements in small regions and in the miniature chemical sensors. For example, when the miniature silver/silver chloride reference electrode of this invention is used, it is possible to integrate a function electrode, a counter electrode and the reference electrode to form a 3-electrode system integrated in a miniature cell formed on a silicon substrate for performing high-precision electrochemical experiment. Also, when it is integrated with ISFET (ion sensing field-effect transistor) or other potentiometric sensor, it is possible to form a one-touch microsensor that can be pierced into a body, such as the human body.

As explained above, for the miniature silver/silver chloride reference electrode in this invention, the stability and durability of the miniature reference electrode are improved, and it can be used in performing electrochemical measurements in small regions and in the miniature chemical sensors. APPLICATION EXAMPLE 4 MICROFABRICATED LIQUID-JUNCTION Ag/AgCl REFRENCE ELECTRODE AND ITS APPLICATION TO A ONE-CHIP POTENTIOMETRIC SENSOR Purpose Microfabricated high-performance reference electrodes are indispensable for putting microchemical sensors into practical application using semiconductor fine processing technology. However, there is no such microfabricated reference electrode which can be used widely in a general manner. The purpose of the present invention is to provide a type of silver/silver chloride reference electrode with liquid junction and good practicability. Also, in order to illustrate its practicability, we have tried to form a microfabricated reference electrode and a pH indicator electrode using an iridium oxide film have been formed in one chip.

Method

A silver/silver chloride thin film had such a configuration that the surface of the silver film was covered with a polyimide layer, and the silver chloride layer was formed from a strip with a width of 50 $\mu$m in the central portion of the thin film (FIG. 1(a)). The silver chloride was formed in a 1M KCl-HCl buffer solution (pH 2.2), and about 80% of the silver was converted to silver chloride. A photocuring ENT-2000 (product of Kansai Paint Co., Ltd.) was used for the liquid junction. An electrolytic layer was formed by screen painting a paste, which was prepared by diffusing KCl fine powder in polyvinylpyrrolidone (PVP) carrier, on the silver layer. An iridium oxide film was used as the pH indicator electrode. The pH indicator electrode was formed by performing potential sweeping in the range of –0.9~+1.1 V (vs. Ag/AgCl) in 1M LiClO$_4$. To incorporate them in one chip, the microfabricated reference electrode and the pH indicator electrode were adhered to each other back to back using a photocuring adhesive (FIG. 6(b)). The microfabricated reference electrode was evaluated based on the standards of the commercially available silver/silver chloride electrode.

Results

The results of evaluating the change in the potential of the microfabricated liquid-junction reference electrode show that the desired potential for silver/silver chloride can be maintained for over 100 h. The potential change is within ±1.5 mV during that period. The PVP layer used as the carrier can suppress dissolution of the silver chloride layer and thus prolongs the service life. Also, the potential of the electrode shows little dependency on pH and the concentration of KCl.

FIG. 11 shows the results of using the microfabricated reference electrode and a commercially available microreference electrode to evaluate the pH dependency of the potential of the indicator electrode after the one-chip sensor is dipped in a 50 mM phosphoric acid buffer solution for 1 h and 25 h. No significant variation in the potential is recognized, which means that the microfabricated reference electrode has excellent practicability.

While preferred embodiments of the invention have been illustrated and described, it is to be understood that various changes may be made therein without departing from the spirit and scope of the invention. Thus, the invention is to be limited only by the scope of the claims that follow and the equivalents thereof.

What is claimed is:

1. A miniature reference electrode, comprising:

a thin-film backbone metal pattern set on an electrode substrate;

a thin-film electrode metal pattern on said thin-film backbone metal pattern and in electrical contact with a portion of said thin-film backbone metal pattern;

a metal salt region on a portion of said thin-film electrode metal pattern and made of a salt of the structural metal of said thin-film electrode metal pattern;

a thin-film electrolyte layer impregnated with a saturated solution of an electrolyte having an anion common with an anion of the metal salt of said metal salt region;

a hydrophobic layer intervening between said metal salt region and said electrolyte layer, said hydrophobic layer having at least one opening which cause a portion of the electrolyte layer to be in contact with the metal salt region; and a thin-film liquid junction pattern in contact with a portion of said thin-film electrolyte layer and impregnated with an electrolyte solution containing the electrolyte of said thin-film electrolyte layer.

2. The miniature electrode of claim 1, further comprising a protective film covering the electrode, at least a portion of said thin-film backbone metal pattern is exposed through the protective film as the electrode terminal portion, and a portion of said thin-film liquid junction pattern is exposed through the protective film as a contact portion with the external liquid.

3. The miniature reference electrode of claim 2 wherein said thin-film electrolyte layer comprises a thin-film electrolyte layer having said electrolyte carried in the form of solid particles.

4. The miniature reference electrode of claim 1 wherein the metal of said thin-film electrode metal pattern is formed of silver, the metal salt of said metal salt region is silver chloride, and the electrolyte of said thin-film electrolyte layer is potassium chloride.

5. The miniature reference electrode of claim 4 wherein the metal of said thin-film backbone metal pattern is gold.

6. The miniature reference electrode of claim 1, further comprising a plurality of holes formed in said thin-film electrode metal pattern, and, as said hydrophobic thin-film insulating layer is bonded with said electrode substrate through said plurality of holes, the adhesion of said thin-film electrode metal pattern on said electrode substrate is increased.

7. The miniature reference electrode of claim 1, further comprising, on the electrode substrate, an auxiliary electrode pattern formed from another metal pattern and a thin-film insulating layer.

8. A one-touch potentiometric sensor comprising,
a miniature reference electrode, said reference electrode comprising:
- a thin-film backbone metal patter set on an electrode substrate;
- a thin-film electrode metal pattern on said thin-film backbone metal pattern and in electrical contact with a portion of said thin-film backbone metal pattern;
- a metal salt region on a portion of said thin-film electrode metal pattern and made of a salt of the structural metal of said thin-film electrode metal pattern;
- a thin-film electrolyte layer impregnated with a saturated solution of an electrolyte of said metal salt region;
- a hydrophobic layer intervening between said metal salt region and said electrolyte layer, said hydrophobic layer having at least one opening which causes a portion of the electrolyte layer to be in contact with the metal salt region;
- a thin-film liquid junction pattern in contact with a portion of said thin-film electrolyte layer and impregnated with an electrolyte solution containing the electrolyte of said thin-film electrolyte layer;
- said potentiometric sensor further comprising a sensor based on the potentiometric measurement principle integrated with the miniature reference electrode.

9. A one-touch electrochemical measurement system comprising:
- a function electrode;
- a counter electrode; and
- a miniature reference electrode integrated on a single chip, the miniature reference electrode comprising:
  - a thin-film backbone metal pattern set on an electrode substrate;
  - a thin-film electrode metal pattern on said thin-film backbone metal pattern and in electrical contact with a portion of said thin-film backbone metal pattern;
  - a metal salt region on a portion of said thin-film electrode metal pattern and made of a salt of the structural metal of said thin-film electrode metal pattern;
  - a thin-film electrolyte layer impregnated with a saturated solution of an electrolyte having an anion common with an anion of the metal salt of said metal salt region;
  - a hydrophobic layer intervening between said metal salt region and said electrolyte layer, said hydrophobic layer having at least one opening which causes a portion of the electrolyte layer to be in contact with the metal salt region; and
  - a thin-film liquid junction pattern in contact with a portion of said thin-film electrolyte layer and impregnated with an electrolyte solution containing the electrolyte of said thin-film electrolyte layer.

10. A method for prolonging the lifetime of a miniature reference electrode made of plural thin-film layers, comprising:
- forming a thin-film electrode metal pattern, with a portion of the thin-film electrode metal pattern formed of a metal salt region made of a salt of the structural metal of the thin-film electrode metal pattern, with the metal salt region exposed on the surface of the thin-film electrode metal pattern;
- forming a thin-film electrolyte layer impregnated with a saturated solution of an electrolyte having an anion common with an anion of the metal salt of said metal salt region, the metal salt region being in contact with a portion of the thin-film electrolyte layer which has said electrolyte carried in the form of solid particles;
- forming a portion of said thin-film electrolyte layer to include a liquid junction exposed to the exterior of the miniature reference electrode; and
- forming a hydrophobic layer intervening between said metal salt region and said electrolyte layer, said hydrophobic layer having at least one opening which provides the contact between the electrolyte layer and the metal salt region.

11. A miniature reference electrode, comprising:
- a thin-film backbone metal pattern set on an electrode substrate;
- a thin-film electrode metal pattern on said thin-film backbone metal pattern and in electrical contact with a portion of said thin-film backbone metal pattern;
- a metal salt region on a portion of said electrode metal pattern and made of a salt of the structural metal of said thin-film electrode metal pattern;
- a thin-film electrolyte layer impregnated with a saturated solution of an electrolyte having an anion common with an anion of the metal salt of said metal salt region;
- a hydrophobic layer intervening between said metal salt region and said electrolyte layer, said hydrophobic layer having at least one opening which causes a portion of the electrolyte layer to be in contact with the metal salt region;
- a thin film liquid junction pattern in contact with a portion of said thin-film electrolyte layer and impregnated with an electrolyte solution containing the electrolyte of said thin-film electrolyte layer; and
- a protective film covering the electrode, at least a portion of the thin-film backbone metal pattern exposed through the protective film as an electrode terminal portion, and a portion of the thin-film liquid junction pattern exposed through the protective film as a contact portion with an external liquid.

* * * * *

UNITED STATES PATENT AND TRADEMARK OFFICE
CERTIFICATE OF CORRECTION

PATENT NO.     : 6,419,809 B1
DATED          : July 16, 2002
INVENTOR(S)    : Hiroaki Suzuki et al.

It is certified that error appears in the above-identified patent and that said Letters Patent is hereby corrected as shown below:

Column 13,
Line 4, "a thin-film backbone metal patter set on" should read -- a thin-film backbone metal pattern set on --.
Line 13, "solution of an electrolyte of said metal" should read -- solution of an electrolyte having an anion common with an anion of the metal salt of said metal --.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,419,809 B1
DATED : July 16, 2002
INVENTOR(S) : Hiroaki Suzuki et al.

It is certified that error appears in the above-identified patent and that said Letters Patent is hereby corrected as shown below:

<u>Title page</u>,
Item [75], the second listed inventor's name should read as -- Isao Karube --.

<u>Column 4</u>,
Line 34, "system is provide, with a function electrode" should be corrected to read as -- system is provided, with an indicator electrode, --.

<u>Column 5</u>,
Line 31, "Example A" should be corrected to read as -- Example 3 --.
Line 42, "(20) was formed" should be corrected to read as -- (29) was formed --.

<u>Column 8</u>,
Lines 1 and 2, "(product of Kansei Paint Co., Ltd.)." should be corrected to read as -- (product of Kansei Paint Co., Ltd.) was used. --.

<u>Column 9</u>,
Line 11, "platinum this film" should be corrected to read as -- platinum thin film --.

Figure 6A:
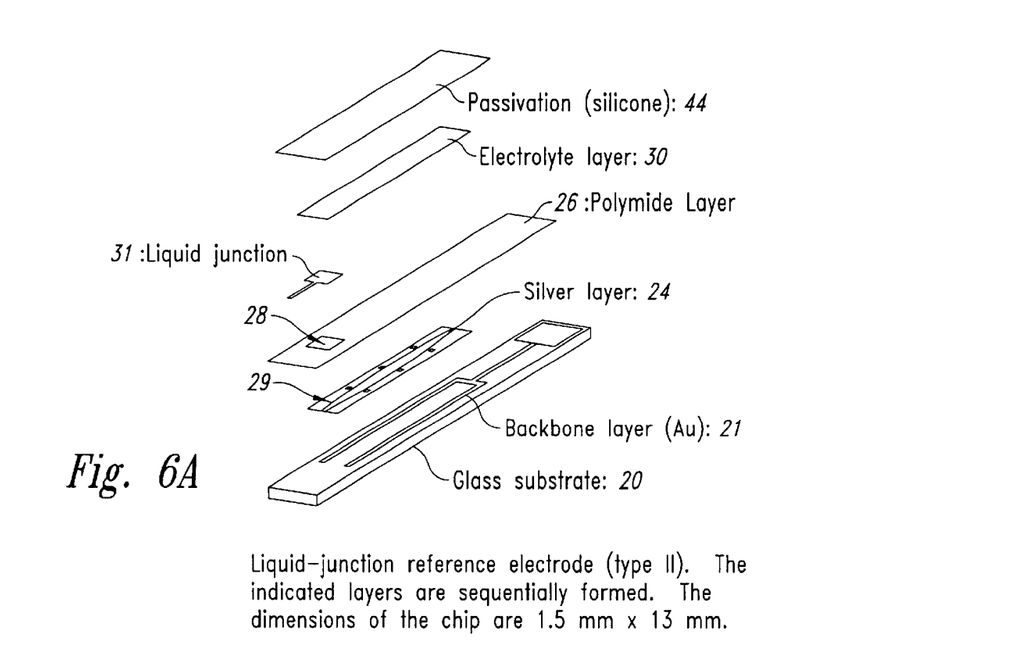
FIGS. 6a and 6b are diagrams illustrating the structure of miniature silver/silver chloride reference electrode of Application Example 1 and application Example A.
Figure 6B:
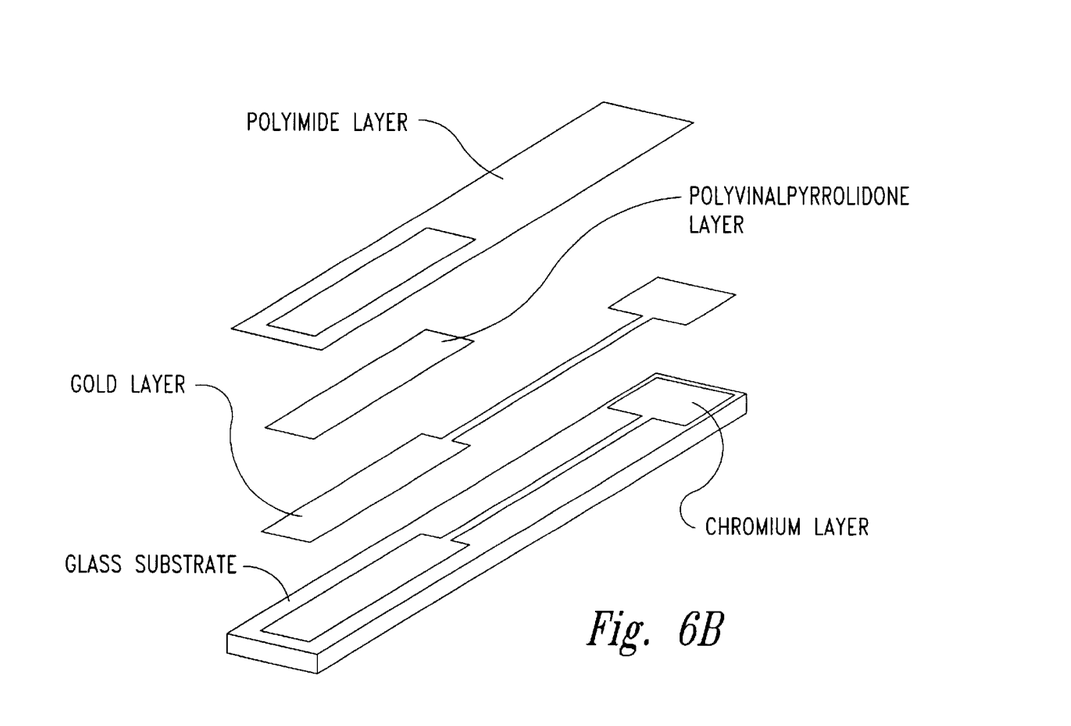

<u>Column 11</u>,
Line 41, "(Figure 1(a))." should be corrected to read as -- (FIG. 6(a)). --.

<u>Column 13</u>,
Line 30, "a function electrode;" should be corrected to read as -- an indicator electrode; --.

Signed and Sealed this

Twelfth Day of August, 2003

JAMES E. ROGAN
*Director of the United States Patent and Trademark Office*